United States Patent

Gilby et al.

[11] Patent Number: 5,900,934
[45] Date of Patent: May 4, 1999

[54] CAPILLARY CHROMATOGRAPHY DETECTOR APPARATUS

[75] Inventors: Anthony C. Gilby, Foxborough; William W. Carson, Hopkington, both of Mass.

[73] Assignee: Waters Investments Limited, New Castle, Del.

[21] Appl. No.: 08/947,455

[22] Filed: Oct. 6, 1997

Related U.S. Application Data

[63] Continuation of application No. 08/602,552, Feb. 20, 1996, abandoned.
[51] Int. Cl.$^6$ .................................................. G01N 21/01
[52] U.S. Cl. ........................................... 356/344; 356/440
[58] Field of Search .................................. 356/344, 436, 356/440

[56] References Cited

U.S. PATENT DOCUMENTS

| 5,003,488 | 3/1991 | Hardy | 356/440 |
| 5,239,360 | 8/1993 | Moring et al. | 356/344 |
| 5,303,021 | 4/1994 | Kita | 356/72 |
| 5,312,535 | 5/1994 | Waska et al. | 204/603 |
| 5,324,401 | 6/1994 | Yeung et al. | 356/344 |

FOREIGN PATENT DOCUMENTS

| 0 437 968 A2 | 7/1991 | European Pat. Off. . |
| 0 476 792 | 3/1992 | European Pat. Off. . |
| 0 581 413 A2 | 2/1994 | European Pat. Off. . |
| 41 39 211 A1 | 11/1990 | Germany . |

*Primary Examiner*—Richard A. Rosenberger
*Attorney, Agent, or Firm*—Brian Michaelis; Anthony J. Janiuk

[57] ABSTRACT

An apparatus to effect multiple simultaneous separations to measure absorbance, comprising a photodetector array comprising a plurality of photosensitive elements connected to provide a serial output. The elements are typically pixels of a photodiode array (PDA). The elements are illuminated by a light source positioned to illuminate at least a portion of the photodetector array. The light source may be a an AC or DC mercury lamp or other useable light source for chromatography. An array of separation channels is disposed between the light source and the photodetector array, each of the separation channels having a lumen, a sample introduction end and a detection region disposed opposite the sample introduction end. Typically and as disclosed herein the array is a multiple parallel capillary electrophoresis system. The last element is a mask element having at least one aperture for each associated separation channel, each aperture corresponding to its associated separation channel thereby selectively permitting light from the light source to pass through the lumen of its associated separation channel, at least a portion of the light passing through the lumen of the associated separation channel falling on a respective photosensitive element of the photodetector array to effect measurement of absorption of light by a sample introduced into the sample introduction end of the associated separation channel. Also disclosed is an instrument for analyzing the spectral content of chemical samples contained in a large number of capillary tubes which uses a single AC powered light source (which therefore gives a time-varying light output) and a single self-scanned PDA detector. This greatly reduces the number of circuit elements required, since only one amplifier, one A/D converter, one light source and one detector need be provided. The resulting device can be constructed less expensively and take up less space as compared to the conventional system. Further, a control signal having a particular frequency is supplied to both the power supply of the AC light source and the PDA detector. This stabilizes the detector signal's baseline.

20 Claims, 6 Drawing Sheets

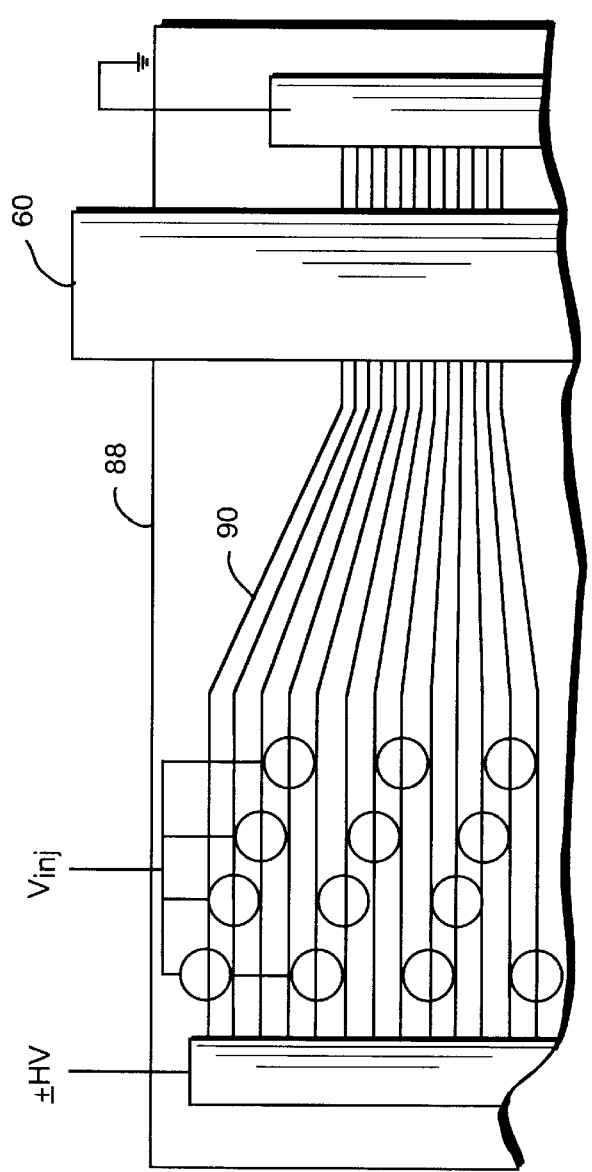

CAPILLARY CHROMATOGRAPHY DETECTOR APPARATUS

This application is a continuation of application Ser. No. 08/602,552 filed on Feb. 20, 1996, now abandoned.

FIELD OF THE INVENTION

The present invention relates generally to the field of capillary electrophoresis in which chemical samples are placed in capillary tubes for analysis of their spectral (frequency information) content and thus their chemical makeup, and more particularly to a photometric apparatus for absorbance detection which enables multiple separations to be measured simultaneously.

BACKGROUND

Capillary electrophoresis ("CE") is a known chemical sample separation technique that is of increasing interest to those concerned with analyzing the separation of the chemical contents of a chemical sample. It is a modification of electrophoresis, and is typically practiced in a thin glass capillary instead of on a 2-dimensional surface such as paper or in a gel. This technique offers the benefits of high efficiency and resolution, rapid separations, the ability to analyze small sample amounts, and a desirable simplicity from the point of view of the apparatus required when compared to competing analytical techniques such as gel electrophoresis, gas chromatography, and liquid chromatography. As in all separation systems, high resolution, sensitivity and dynamic range are the end objectives.

The benefits of capillary electrophoresis derive to a large extent from the use of narrow diameter capillary tubes, which permit efficient removal of the heat generated in the separation process. This heat removal prevents convective mixing which would degrade the separating power. The narrow diameter tubes also allow high voltages to be used to generate the electric field in the capillary while limiting current flow and hence heat generation.

A CE separation begins by filling the capillary with a supporting electrolyte. Next, a small amount of sample is injected into one end of the capillary. Typical sample injection volumes range from 1–20 nanoliters. After sample injection, and with each end of the capillary immersed in a buffer solution, a high voltage is applied to the capillary and the sample components are separated on the basis of different ion mobility. A capillary electrophoretic separation can also be augmented with a bulk fluid flow, called electro-osmotic flow. If present, it adds a constant-velocity component to all species in the capillary.

In a CE separation implementing absorption techniques, the contents of the capillary tube are then analyzed by passing light of a certain wavelength through the capillary tube and then detecting the amount of light which has passed through the tube using a photodetector. The wavelength used is chosen to coincide with an absorption band of the sample components of interest, usually in the ultraviolet or visible regions of the spectrum. The photodetector output is digitally processed and used to compute the absorbance of the sample. An electropherogram, i.e. the plot of absorbance versus time, is typically stored in a computer file and may be displayed on, for example, a PC screen.

With conventional systems if a plurality of capillary tubes are to be used, a corresponding number of light sources, photodetectors, amplifiers and A/D converters must also be used. The outputs of the plurality of A/D converters are fed into signal processing circuitry such as a Digital Signal Processing chip to time average the data, compress it and send it to a personal computer for storage and/or display.

It has become very practical and desirable to use a plurality of capillary tubes in parallel, since this enables more samples to be analyzed at the same time. However, using the conventional systems described above results in a very expensive and large-sized assembly since much duplication of circuitry is necessary. For each capillary tube in the parallel configuration, the apparatus requires a corresponding D.C. light source, photodetector, amplifier and A/D converter. Such redundancy of components disadvantageously impacts, among other things, the cost and size of such parallel analytical instruments.

An example of a known multiple capillary electrophoresis separation system using absorbance detection is disclosed in European Patent Application 0 581 413 A2. In the disclosed apparatus, light from a light source is directed to the measurement region of each capillary, using a plurality of optical fibers. A second set of optical fibers routes transmitted light to a plurality of photo detectors, each of which has its own amplifier and signal processing electronics. The optical fiber configuration results in complexity, light loss and reduced analytical sensitivity. Additionally, as discussed, such an implementation disadvantageously has numerous redundant components.

Another example of multiple capillary electrophoresis is provided in U.S. Pat. No. 5,324,401 which employs fluorescence detection. In this invention, a continuous source of light from a coherent light source, a laser, is delivered to a plurality of optical fibers, each one delivering excitation light to a respective separation capillary. The measurement regions of the capillaries are arranged adjacent to each other such that emitted fluorescent light can be imaged using a CCD camera. It should be noted that lasers do not generally have the required stability for absorbance measurements, are much more expensive, and less suitable for use in routine analytical apparatus. In addition, suitable lasers do not exist with wavelengths near the absorption maximum of many analytes. Furthermore, a CCD camera generally is not a suitable choice as a detector for an absorbance measurement because for absorbance, light levels are typically high and lead to saturation of the CCD pixels before they can be read out. Reducing the light source output to suit the CCD detector results in reduced analytical sensitivity and dynamic range. Fluorescence measurements, in contrast, are low light level measurements, well matched to the characteristics of a CCD detector.

Another class of multiple capillary separations are referenced and their limitations critiqued in U.S. Pat. No. 5,324,401. The referenced systems use detection implementations where the measurement region of each capillary is scanned sequentially. Typically, a confocal method is used to sequentially measure laser excited fluorescence from an array of separation capillaries. The numerous disadvantages of such systems include, as applied to absorption measurements as discussed hereinbefore, the limitations of a laser beam as a light source, and relatively greater expense associated with complex optics.

SUMMARY OF THE INVENTION

A first preferred embodiment of the invention is an apparatus to effect multiple simultaneous separations to measure absorbance, comprising a photodetector array comprising a plurality of photosensitive elements connected to provide a serial output. The elements are typically pixels of a photodiode array (PDA). The elements are illuminated by a light source positioned to illuminate at least a portion of the photodetector array. The light source may be a an AC or DC mercury lamp or other useable light source for chromatography. An array of separation channels is disposed between the light source and the photodetector array, each of the separation channels having a lumen, a sample introduction end and a detection region disposed opposite the sample introduction end. Typically and as disclosed herein the array is a multiple parallel capillary electrophoresis system. The last element is a mask element having at least one aperture for each associated separation channel, each aperture corresponding to its associated separation channel thereby selectively permitting light from the light source to pass through the lumen of its associated separation channel, at least a portion of the light passing through the lumen of the associated separation channel falling on a respective photosensitive element of the photodetector array to effect measurement of absorption of light by a sample introduced into the sample introduction end of the associated separation channel.

According to the present invention, an instrument for analyzing the spectral content of chemical samples contained in a large number of separation channels or capillary tubes uses a single light source and a single self-scanned photodiode array ("PDA") detector. This greatly reduces and simplifies the number of circuit elements required, since only one amplifier, one A/D converter, one light source and one detector need be provided. The resulting device can be constructed less expensively and take up less space as compared to known multiple separation systems.

In further accord with the present invention, the single light source is AC powered and the frequency of the AC light source's power supply is locked to the PDA clock so that each detector element or pixel of the PDA will see exactly the same number of light source cycles, including any partial cycles at the start and end of the exposure period. This dramatically improves the detector signal baseline stability.

In still further accord with the invention, each separation channel is a capillary in an array of separation capillaries and includes a masked portion that confines impinging light to a desired detection region.

Features of the invention include an analytical instrument that can be produced for lower cost and which provides a highly reliable and stable analysis. In a capillary electrophoresis ("CE") embodiment, high throughput CE is effected in a device that is of a reasonable size. The single light source and detector array facilitate flexibility in the number of capillaries that can be simultaneously analyzed. The CE embodiment of the present invention combines the advantages of CE and highly stable absorbance detection with the high throughput of parallel analysis, in a system that is relatively low cost and relatively compact in comparison to known parallel CE systems.

BRIEF DESCRIPTION OF THE DRAWINGS

FIGS. 6 and 6a are an illustrative alternative embodiment of separation channels etched into a planar substrate.

DETAILED DESCRIPTION OF THE PREFERRED EMBODIMENTS

Figure 1:
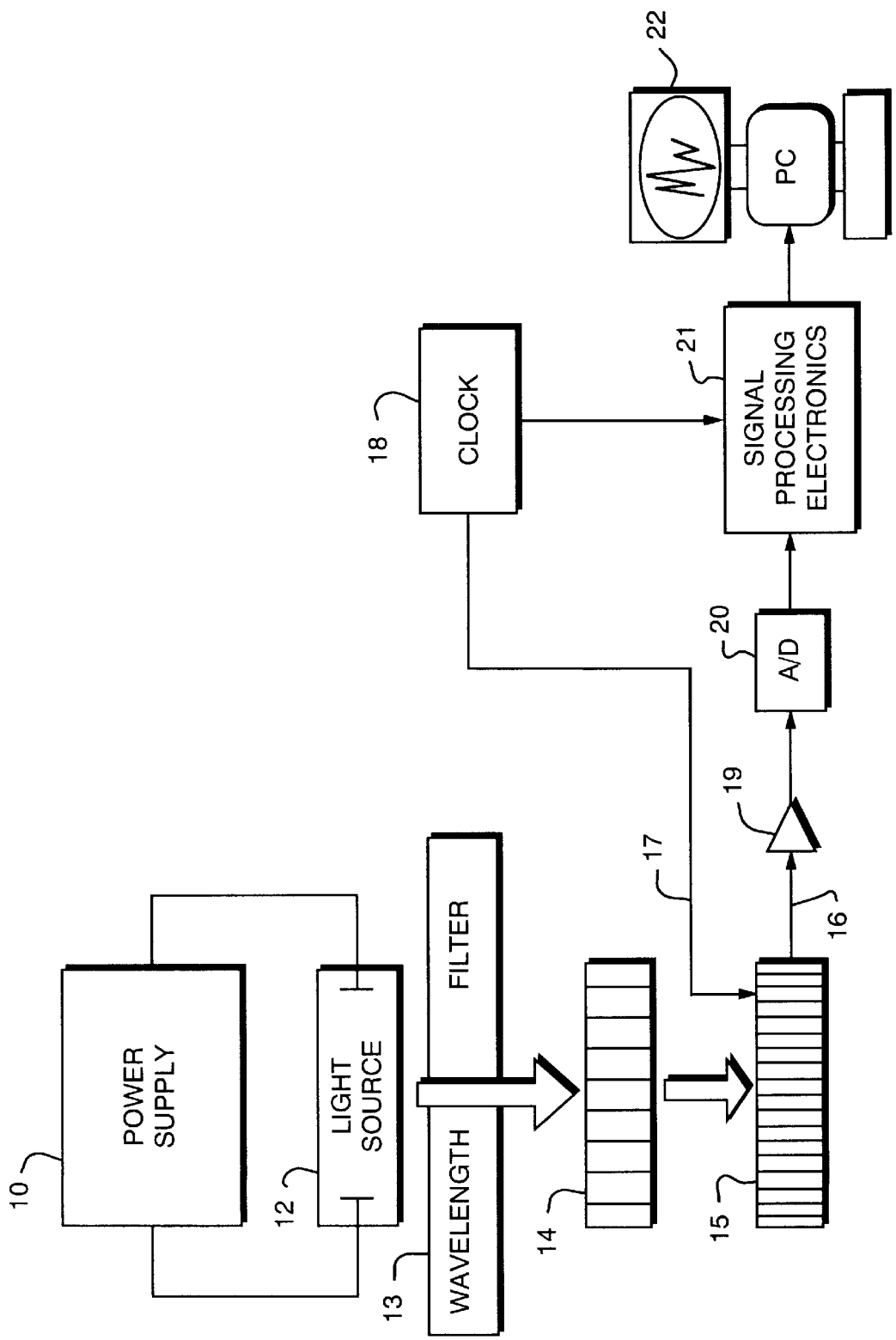
FIG. 1 is a block diagram of a first preferred embodiment of the present invention.
Figure 2:
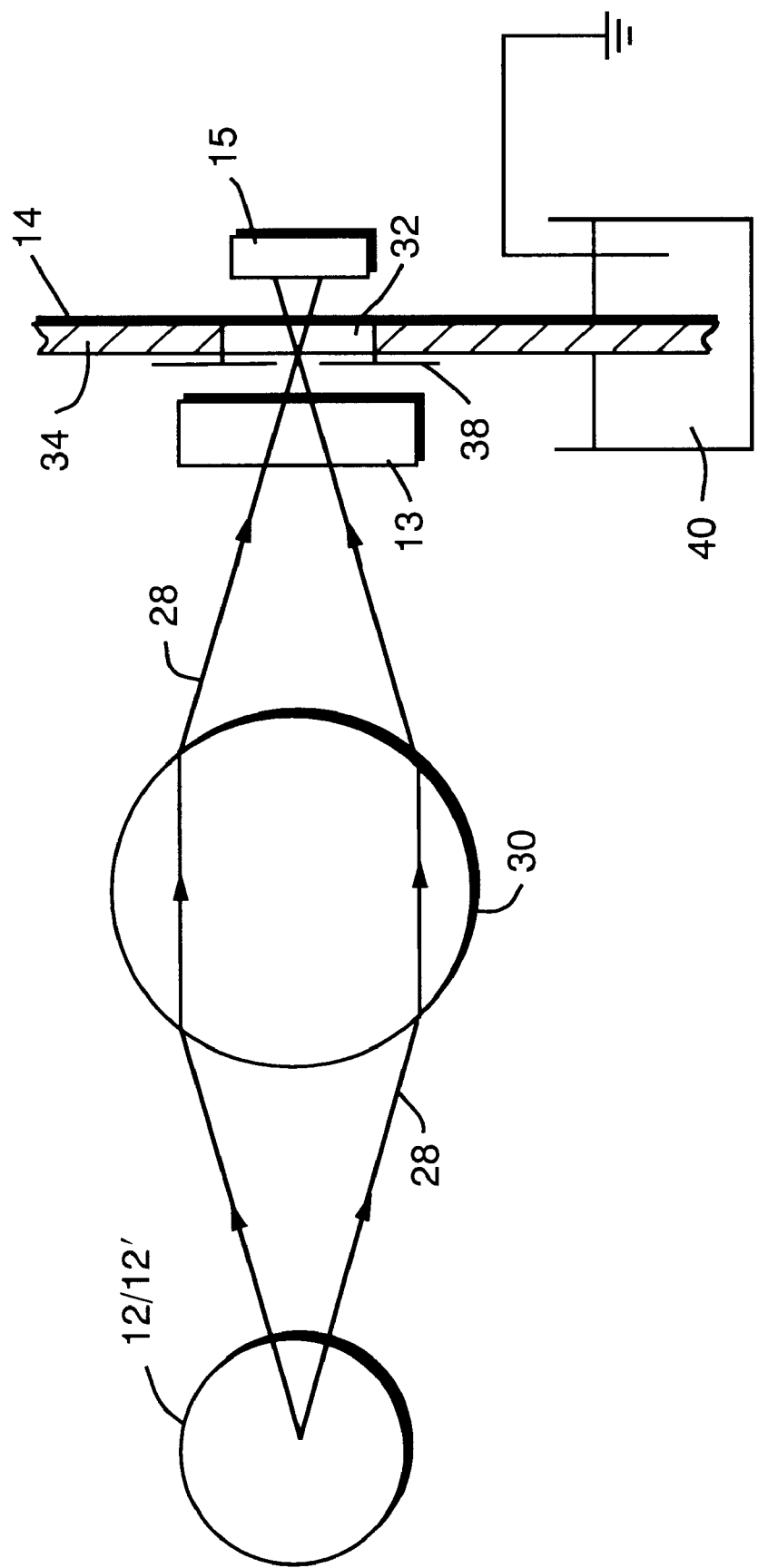
FIG. 2 is a diagrammatic side view of optics implemented in an illustrative embodiment of the present inventions.
Figure 3:
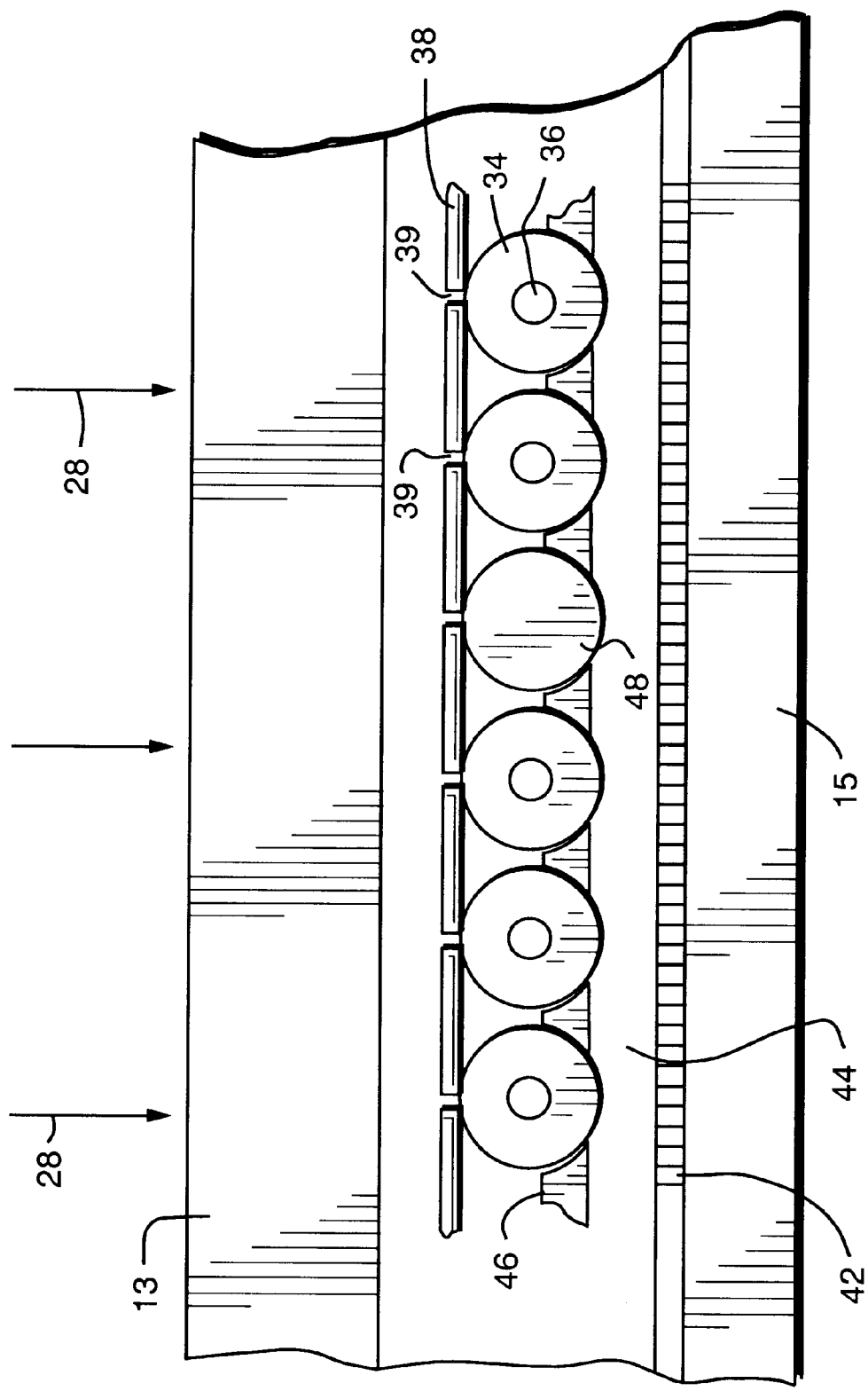
FIG. 3 is a top down diagrammatic view of a capillary array implemented in an illustrative embodiment of the present inventions.
Figure 4:
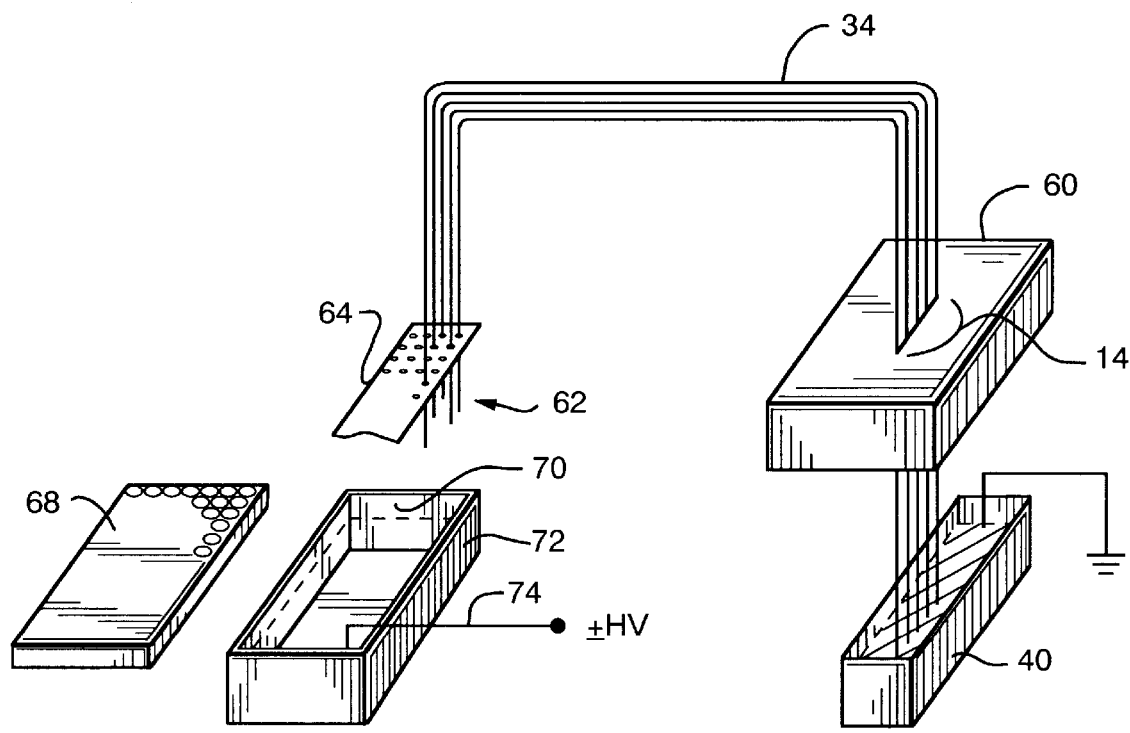
FIG. 4 is a perspective view of a multiple parallel capillary electrophoresis illustrative embodiment according to the inventions.

Two preferred embodiments of the invention are shown in FIGS. 1 through 4, as applied to a parallel capillary electrophoresis ("CE") apparatus. FIG. 1 depicts a first preferred embodiment of the invention, an apparatus to effect multiple simultaneous separations to measure absorbance, comprising a photodetector array 15 comprising a plurality of photosensitive elements 42 (FIG. 3) providing a serial output. The elements are typically pixels of a photodiode array (PDA). The elements are illuminated by a light source 12 positioned to illuminate at least a portion of the photodetector array 15. The light source may be a mercury lamp or other useable light source for chromatography and may be either AC or DC powered. An array of separation channels 14 is disposed between the light source 12 and the photodetector array 15, each of the separation channels 34 having a lumen 36, a sample introduction end and a detection region disposed opposite the sample introduction end. Typically and as disclosed herein the array is a multiple parallel capillary electrophoresis system having capillaries 34 as shown in FIG. 4. The last element is a mask 38 (FIG. 2) having at least one aperture 39 for each associated separation channel, each aperture corresponding to its associated separation channel thereby selectively permitting light from the light source 12 to pass through the lumen of its associated separation channel, at least a portion of light passing through the lumen of the associated separation channel falling on a respective photosensitive element of the photodetector array 15 to effect measurement of absorption of light by a sample introduced into the sample introduction end of the associated separation channel.

Figure 1A:
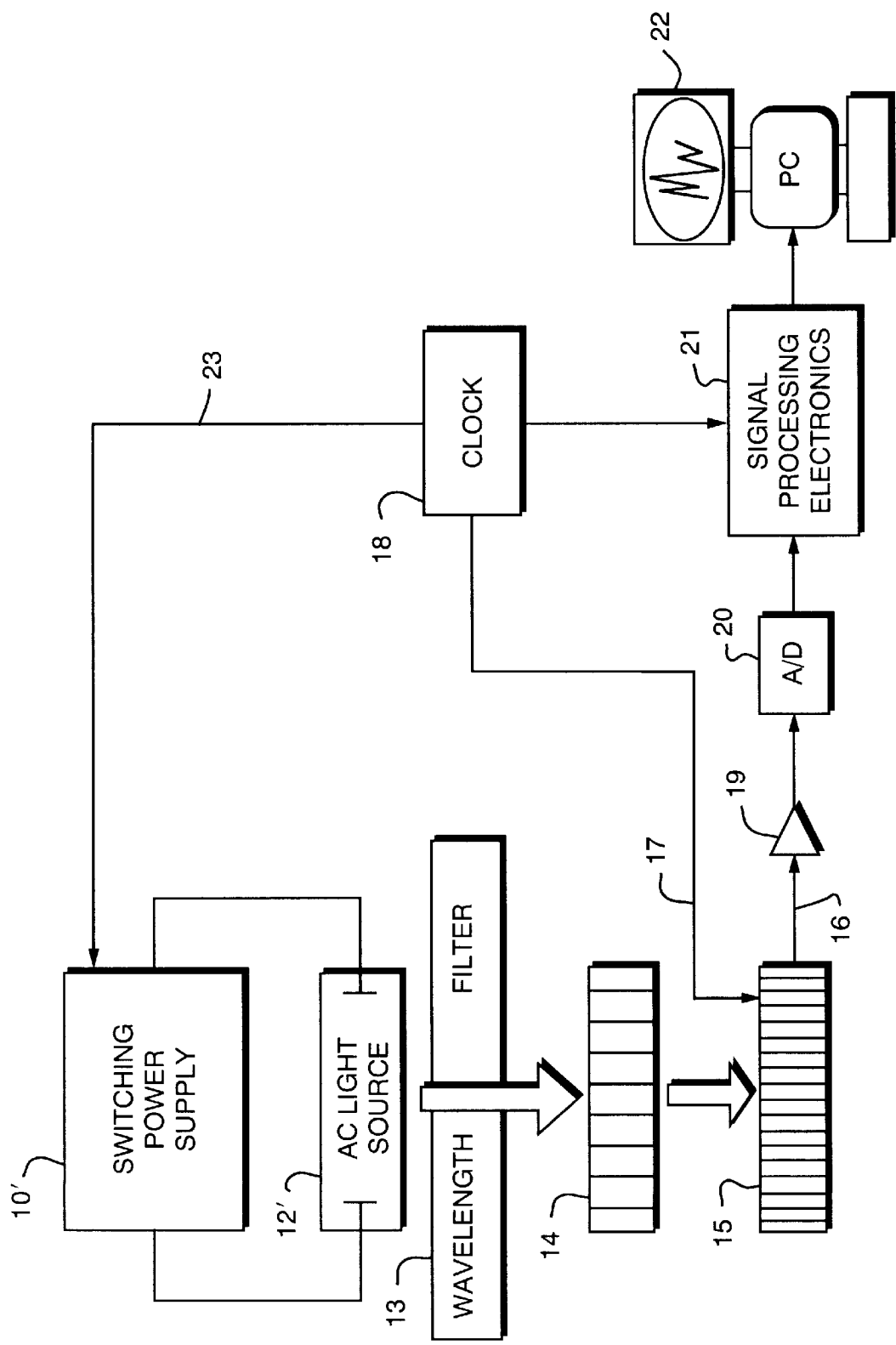
FIG. 1A is a block diagram of a second preferred embodiment of the present invention.

A second preferred embodiment is directed to a specific application of a phase-locked AC power source for the light source and is shown in FIG. 1A. A switching power supply 10' supplies AC power to an AC (or pulsating) light source 12'. In the present illustrative embodiment, the light source is a single, low pressure mercury lamp, which must be AC powered to work properly, and which emits light at a number of discrete wavelengths. The mercury lamp is an extended light source capable of illuminating a parallel array of separation channels or capillaries simultaneously. A narrow bandpass filter 13 is used to select an analytical wavelength, such as 254 nm, which coincides with sample absorption. Other wavelengths of light that are not within the selected narrow band are filtered out by the wavelength filter 13.

While the single light source described herein is an AC powered mercury lamp, it will be appreciated that other direct or indirect light sources, powered by AC or DC can be implemented according to the invention, such as a Zinc, Cadmium, Xenon or, Deuterium arc, or a pulsed laser or the like.

The selected wavelength light beam from the single light source passes through the filter 13 and impinges upon separation channels in the form of a parallel array 14 of capillary tubes, each containing a chemical sample being analyzed. The samples in these tubes absorb light to varying amounts depending on the chemical make-up of the samples. The separation channels implemented in this illustrative embodiment comprise a capillary tube array 14 that includes 48 capillaries 34 configured in parallel to share the same light source. The capillaries are coated or otherwise masked to block out light. Each of the capillaries 34 in the array includes an aperture 39 which provides a window for light to traverse the capillary lumen 36. In this illustrative embodiment, a thin metal mask with chemically machined slits prevents light rays from passing through the walls of the capillaries or between the capillaries. Other masking means are possible and will generally be a function of the separation application. The selected wavelength of light is concentrated in a line image at the location of the apertures to facilitate absorbance detection.

FIG. 2 illustrates the optical system that may be implemented according to the invention to direct the selected wavelength(s) of light. Light rays 28 from extended, AC powered light source 12' are collected by a fused silica rod lens 30 and focused through wavelength filter 13 into a line image on the capillary array 14, seen edge-on in this view. A section of polyimide coating is removed from the area forming the aperture or a detection region 32 of each capillary tube 34. Mask 38 allows light rays which pass through each capillary lumen 36 (shown in detail in FIG. 3) to reach photosensitive elements, i.e. pixels 42 of a PDA detector 15. Pixels midway between capillaries receive essentially no light. The exit ends of capillaries 34 terminate in electrolyte buffer reservoir 40 which is typically at the ground potential of the electrophoretic power supply (not shown).

FIG. 3 shows the capillary array 14 and mounting and masking arrangement in greater detail. Capillaries 34 are located in a set of V-grooves 44 in mounting plate 46, which is machined to provide apertures for the light to pass in the detection region 32. At intervals, e.g. approximately every 10 capillaries, a fused silica optical fiber 48, with polyimide coating removed, is inserted. These provide reference channels to allow the absorbance measurements of each analytical channel to be corrected for light source noise and drift.

Light, of the selected wavelength, which is not absorbed by the chemical sample being analyzed, will pass through the sample array 14 and impinge upon photosensitive elements of the PDA detector 15. The PDA detector 15 detects the amount of light passing through the sample array 14 and accumulates a corresponding amount of charge in each element or pixel of the detector array 15. In this illustrative embodiment an EG&G 512 element monolithic self scanning linear photodiode array is implemented. The detector array 15 is more fully described in the EG&G RETICON T Series Solid State Line Scanners Application Notes, which are incorporated herein by reference. An accumulated charge on each sensor element is shifted sequentially onto the output video line 16 when a shift control signal is received over a line 17 from a clock 18.

The serial charge output is provided to an amplifier 19 which increases the magnitude of the signal to a meaningful level. The output of amplifier 19 is then supplied to an A/D converter 20 for converting the analog signal to a digital signal.

The digital signal output from AID converter 20 is supplied to known signal processing circuitry 21 (such as a DSP chip) which performs processing functions on the data such as time averaging and reducing the number of data samples. The clock 18, which controls the PDA detector 15, also provides a timing control signal to the signal processing circuitry 21. The processed results output from signal processing circuitry 21 are sent to a personal computer (PC) 22 or other computational device for storage or display of the spectrographic results for analysis by the scientist.

In systems wherein a light source is powered by an AC current so that the light output is modulated at double the AC frequency, there is no relationship between the light source frequency and the photodetector clock. Without correction, a pixel may see a fractionally different number of light cycles from one charge accumulation period to the next. This will result in a change in the output signal, even though the average power of the light falling on the detector is unchanged. Accordingly, the instrument baseline will be noisy. In the worst case, as the light source and PDA frequencies drift in and out of phase relative to each other, the baseline may be seriously corrupted by lower frequency beats.

Thus, in accordance with the second preferred embodiment of the invention, the frequency of the AC light source's power supply is locked to the PDA clock so that each pixel will see exactly the same number of light source cycles, including any partial cycles at the start and end of the exposure period. The clock 18 which supplies the shift control signal to the PDA detector array 15, via an electrical line 17, also supplies a control signal to the switching power supply 10 via another electrical line 23. The clock 18 supplies these two control signals at the same frequency. Therefore, the switching power supply 10 and the PDA detector array 15 are both driven at the same frequency. This dramatically improves the detector signal baseline stability.

It will be appreciated, however, that in certain applications and configurations, the frequency of the light source power supply and the frequency at which the PDA is driven may be exact multiples of each other. Alternatively, the two frequencies may be selected so that the difference therebetween assures no low frequency beats. That is, the frequency of harmonic induced distortion is outside the bandwidth of the system.

In operation, the illustrative embodiment of the present invention provides a multiple parallel CE apparatus where a single AC mercury lamp illuminates the row of 48 capillary tubes at a single wavelength, e.g. 254 nm. The 512 element photodiode array positioned behind the capillary tubes measures the light passing through each capillary lumen. Several adjacent photodiode elements collect light from a respective capillary, and their outputs are summed together to constitute one of the parallel electropherograms associated with the respective capillary.

The individual photodiodes in the PDA 15 accumulate charge for a fixed length of time before the charge is transferred to a serial output port. Thereafter, the charge is amplified and A/D converted to provide the measurement. In the illustrative photodiode array detector, the controlling clock frequency is 50 kHz, and one of the diode elements is read and reset to begin charge accumulation anew every 20 microseconds. Thus, the 512 element detector is completely scanned and reset in just over 10 milliseconds. The array is scanned again after a delay to allow charge accumulation to occur. Optimally, the time delay is chosen for the pixels generating the most photocurrent to acquire a charge close to, but below, saturation. It is important to note that in a related series of measurements (e.g. for the period of a CE separation) the time delay is the same whole number of clock cycles in order that the accumulation time does not vary from scan to scan.

In most cases where an AC powered arc lamp is used, the photodetector will measure the light signal continuously with a time constant very long compared with the lamp power supply frequency. This will effectively average the lamp fluctuation cycles to give a constant output.

A further functional illustration of the embodiment of a multiple parallel capillary electrophoresis system according to the present invention is shown in FIG. 4. The self-scanned photodiode array detector 15, which is depicted in greater detail in FIGS. 2 and 3, is diagrammatically represented as a module 60 in FIG. 4. The individual capillaries 34 of capillary array 14 are separated at a sample introduction end 62 using a holder 64. Only a portion of holder 64 is shown in FIG. 4 for clarity. An exit end of the capillary array 14 terminates in an electrolyte buffer reservoir 40, maintained at ground potential.

At the start of an analysis, holder 64 is positioned so that the sample introduction end 62 of capillaries 34 are immersed in sample(s) in the individual wells of a microtiter plate 68. In the illustrative embodiment, capillary array 14 contains 48 separation capillaries 34, and can simultaneously sample half the wells in a standard 96-well microtiter plate. Hydrostatic sample introduction is effected in a conventional manner by raising the height of microtiter plate 68 and holder 64 above that of the buffer reservoir 40 for a few seconds. Following sample introduction, the microtiter plate 68 and capillary holder 64 are lowered, and the ends 62 of capillaries 34 placed in running buffer electrolyte 70 in an electrolyte container 72. The level of the electrolyte in containers 72 and 40 is held the same during separation. High voltage is applied to electrode 74 which contacts electrolyte 70. Positive or negative high voltage is used depending on the species to be separated.

As electrophoresis proceeds, separated species pass through the detection region 32 of capillaries 34 (illustrated in FIG. 3) and a signal proportional to the light transmitted through each capillary is output in serial fashion, for example, every 15 milliseconds.

Figure 5:
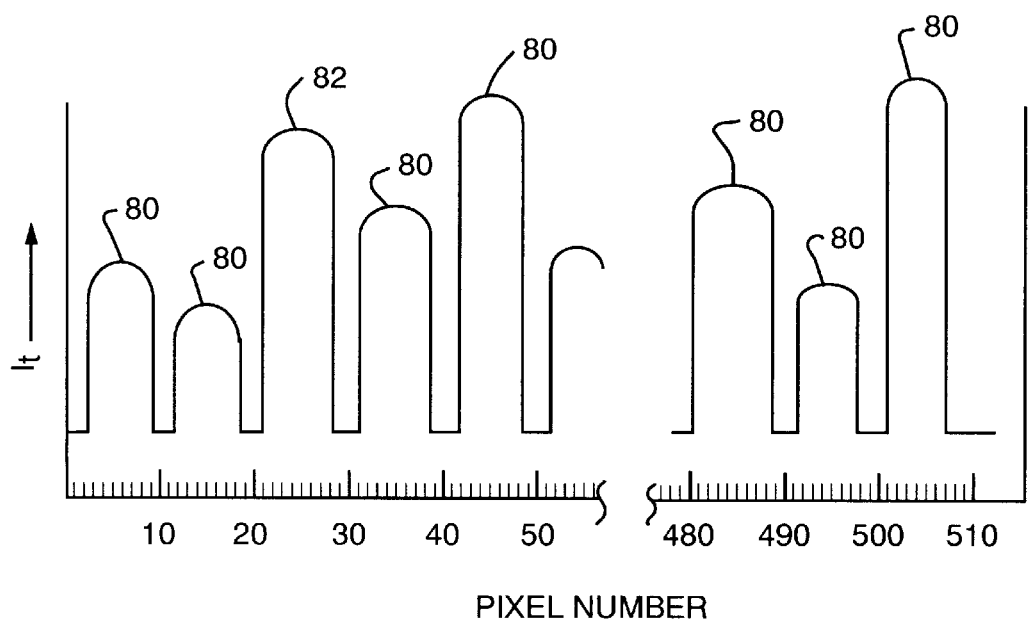
FIG. 5 is a graphical illustration of sample data collected from a single scan of the embodiment of FIG. 4.

FIG. 5 illustrates a sample of data collected from a single scan (or average of several scans) of photodiode array 15. Each pixel on the PDA accumulates photo charge between scans. When the device is scanned, all the charge packets are switched sequentially onto the video line (16 in FIG. 1). The charge packets are amplified and converted to a digital value. In the illustrative embodiment, the PDA has 512 pixels divided into 48 analytical channels 80, each channel corresponding to a respective capillary of the separation capillaries 34. In addition, in this illustrative embodiment, there are three reference channels 82, corresponding to reference optical paths 48, (FIG. 3). One reference optical path is located in the middle, and one near each end of the array. FIG. 5 illustrates a plot of the raw signal It or It(ref) (as discussed hereinafter), for each pixel in the array.

A group of 7 or 8 pixels receives light corresponding to one channel, and there are two or three pixels between channels which receive very little light and whose signals are ignored.

To more easily understand the signal processing needed to compute absorbance in an analytical channel, consider a single pixel (a sample pixel) receiving light through the detection region of one of the separation capillaries, and a pixel receiving light through one of the reference channels. For purposes of this illustration:

$I_t$ is the sample pixel signal at time t;

$I_0$ is the sample pixel signal at time zero (the start of a separation)

$I_d$ is the dark signal measured with the lamp off, or its light blocked.

$I_{t(ref)}$, $I_{0(ref)}$ and $I_{d(ref)}$ are analogous signals from the reference pixel.

Absorbance is calculated from:

$$A = log_{10}\{[(I_0-I_d)/(I_t-I_d)]\cdot[(I_{t(ref)}-I_{d(ref)})/(I_{0(ref)}-I_{d(ref)})]\}$$

The purpose of the reference channels is to compensate for changes in light source output during a separation run. The second quotient in the expression above modified the $I_0$ value to correct for such fluctuations, which would otherwise increase the noise and drift on the baseline.

In practice, signals from pixels corresponding to the same separation or reference channel will be combined to improve the signal-to-noise ratio of the analytical measurement.

The time course of absorbance for each separation channel is the desired electropherogram, and contains the desired analytical information.

It will be appreciated that separation channels other than discrete capillaries in an array can be implemented to effect the separation system according to the invention. FIGS. 6 and 6a illustrate that the separation channels can alternatively be implemented as etched channels 90 in a planar structure 88. An etched silica plate 92 is bonded to a silica substrate 94 to form a structure 88 suitable for parallel separations by electrophoresis. Samples are introduced into wells 96 and buffer electrolyte into wells 98 and 100. Sample injection is effected by briefly applying a voltage Vin to all sample wells in parallel. Separation is effected by applying the high voltage (+/− HV) between the electrolyte wells. A light source and array photodetector of the present invention 60 are used to measure sample absorption. Light is prevented from passing between separation channels by disposing an opaque material onto one of the silica plates, adjacent to the channels, before bonding. Appropriate openings in the mask can be used to create reference channels.

Although the apparatus described hereinbefore has light from a single source passing through a wavelength filter to impinge on a plurality of capillaries, it may be appreciated that the configuration may also include optics, as part of the wavelength filter or otherwise, to focus the light beams from the single source more precisely onto the array of capillaries. Optics may be used to image the array of capillaries onto a mask or onto the PDA.

While the capillary array described in the illustrative embodiment according to the invention is implemented with 48 capillaries, it will be appreciated that fewer or greater numbers of parallel separations can be effected in the flexible single light source/detector array configuration. Furthermore, it will be appreciated that a single light source can be used in conjunction with opposed PDA's each having an array of parallel capillaries disposed between the light and a respective PDA to effect a dual array implementation. In such an implementation, all 96 wells in a standard microtiter plate can be analyzed simultaneously.

Likewise, it will be appreciated that the capillary array can be implemented with a larger or smaller number of interspersed reference channels, such as optical fibers disposed at intervals, to effect a feedback mechanism for monitoring and adjusting for lamp fluctuations, and that the fibers, although illustrated herein as being disposed parallel to the capillaries, can be alternatively oriented to collect light, such as being perpendicularly disposed.

Although the illustrative embodiment described hereinbefore uses an EG&G 512 pixel self scanned photo diode array to detect light passing through the subject capillary array, it should be appreciated that higher or lower resolution detector devices from EG&G or from other manufacturers can be implemented. For example, a Hamamatsu linear image sensor S3904 has 1024 pixels, each 25 micrometers wide. Similarly, alternative photodetection mechanisms can be implemented such as charge coupled devices (CCD), charge injection devices (CID) or the like.

Furthermore, while the embodiment described hereinbefore relates to a single wavelength light source and array detector for parallel CE separations using multiple capillaries, it should be appreciated that the single light source/detector combination could similarly be used in other applications, including: multiple separation channels that are etched in glass or a silicon substrate; electrokinetic chromatography in a multiple parallel separation format (e.g. plural electro-osmotically pumped mobile phases with respective packed beds, or equivalent micromachined columns); multiple parallel capillary liquid chromatography systems, or the like.

Equivalents

Those skilled in the art will recognize, or using no more than routine experimentation, equivalents to the specific embodiments of the invention described specifically herein. Such equivalents are intended to be encompassed in the scope of the following claims.

We claim:

1. A chemical sample analysis apparatus comprising:
   an AC light source;
   an AC power supply connected to said AC light source;
   a photodetector array;
   a detector scanning clock controlling said photodetector array, said AC power supply and said detector scanning clock being phase locked to each other by one of, said AC power supply being substantially equal in frequency to said detector scanning clock, or one of said detector scanning clock and said AC power supply being a fixed multiple of the other of said detector scanning clock and said AC power supply; and
   means to hold an array of samples disposed between said AC light source and said photodetector array.

2. The apparatus of claim 1 wherein said photodetector array is made up of a plurality of photosensitive elements connected to a serial output line of said photodetector array.

3. The apparatus of claim 2 further comprising an amplifier and an A/D converter connected to said serial output line of said photodetector array.

4. The apparatus of claim 1 wherein said array of samples are contained in capillary tubes.

5. The apparatus of claim 1 wherein said array of samples is configured in an array of capillary tubes including a mask portion which substantially blocks light from said light source, which light has not passed through said array of samples, from reaching said photodetector array.

6. The apparatus of claim 1 further including a filter disposed between said AC light source and said photodetector array, for selecting at least one wavelength of light from said AC light source.

7. The apparatus of claim 1 further including optics to focus said light from said AC light source to impinge upon said array of samples in a predetermined manner.

8. The apparatus of claim 1 wherein said array of samples includes at least one reference channel.

9. The apparatus of claim 8 wherein said at least one reference channel includes a length of optical fiber.

10. An apparatus for determining the presence or absence of an analyte comprising:

a) means for holding a containment vessel, said containment vessel for containing a sample in which the analyte may be present or absent;

b) a light source capable of producing pulsed light when powered by an alternating current, said light source in communication with said containment vessel, said alternating current having a frequency which causes light to be at said frequency or multiple of said frequency;

c) a photodetector array having one or more pixels in optical communication with said containment vessel and said light source, for receiving light from said light source through said containment vessel and the sample contained therein, said photodetector array having a scanning frequency in which electrical discharge signals are received from said pixels; and d) a clock control for controlling the frequency of at least one of the frequencies of said scanning frequency and said alternating current frequency such that at least one frequency is a multiple of the other or said frequencies are equal, said photodetector array receiving light from said light source through said containment vessel and sample contained therein to measure absorbance over a period of time comprising a plurality of electrical discharge signals, said pixels are scanned at a frequency corresponding the frequency of said alternating current and said electrical discharge signals generated at constant light intensity to reduce baseline variability of said electrical discharge signals over a period of time comprising a plurality of electrical discharge signals.

11. An apparatus for determining the presence or absence of an analyte, in a plurality of samples, each sample held in separate separation channels, comprising:

a) a planar housing having a plurality of separation channels, each separation channel having a lumen for containing a sample in which the analyte may be present or absent, said planar housing having a mask element having one or more optical openings associated with each separation channel to selectively allow light from a light source to pass through said lumen;

b) a light source capable of producing light, said light source in communication with the lumen of each separation channel through said one or more optical openings of said mask element;

c) a photodetector array having one or more pixels in optical communication with the lumen of said separation channel and said light source, for receiving light from said light source through the lumen of said separation channel and the sample contained therein, said photodetector array producing electrical discharge signals serially from said pixels with are related to the absorbance of light by the sample therein.

12. The apparatus of claim 11 wherein said apparatus further includes a signal processor receiving said serial-output and computing absorbance as a function of the measurement of absorption of light by said sample.

13. The apparatus of claim 11 wherein said separation channels are etched into a planar substrate.

14. The apparatus of claim 11 wherein said separation channels are implemented as separation capillaries.

15. The apparatus of claim 11 wherein said photodetector array is a self-scanned photodiode array.

16. The apparatus of claim 11 wherein said light source is powered by an AC power supply and said photodetector array is a self-scanned photodiode array driven by a detector scanning clock.

17. The apparatus of claim 16 wherein said AC power supply and said detector scanning clock are phase locked to each other by one of, said AC power supply being substantially equal in frequency to said detector scanning clock, or one of said detector scanning clock and said AC power supply being a fixed multiple of the other of said detector scanning clock and said AC power supply.

18. The apparatus of claim 11 further including a wavelength filter disposed between said light source and said photodetector array.

19. The apparatus of claim 11 wherein said array of separation channels includes at least one reference channel, free of sample, interspersed among said array of separation channels.

20. The apparatus of claim 11 wherein said at least one reference channel includes a length of optical fiber.

* * * * *